United States Patent
Lee

(10) Patent No.: US 8,606,045 B2
(45) Date of Patent: Dec. 10, 2013

(54) IMAGE BASED REGISTRATION USING TRANSFORM AND SECOND IMAGES OF A TARGET OBJECT

(75) Inventor: Kwang Hee Lee, Seoul (KR)

(73) Assignee: Medison Co., Ltd., Kangwon-do (KR)

(*) Notice: Subject to any disclaimer, the term of this patent is extended or adjusted under 35 U.S.C. 154(b) by 367 days.

(21) Appl. No.: 12/628,861

(22) Filed: Dec. 1, 2009

(65) Prior Publication Data

US 2010/0135599 A1 Jun. 3, 2010

(30) Foreign Application Priority Data

Dec. 2, 2008 (KR) .................. 10-2008-0121461
Jul. 20, 2009 (KR) .................. 10-2009-0065664

(51) Int. Cl.
*G06K 9/32* (2006.01)
*A61B 5/05* (2006.01)

(52) U.S. Cl.
USPC .......................................... 382/294; 600/407

(58) Field of Classification Search
USPC ................................................... 382/294
See application file for complete search history.

(56) References Cited

U.S. PATENT DOCUMENTS

| | | | | |
|---|---|---|---|---|
| 7,117,026 | B2* | 10/2006 | Shao et al. | 600/411 |
| 2006/0004274 | A1* | 1/2006 | Hawman | 600/407 |
| 2006/0004275 | A1* | 1/2006 | Vija et al. | 600/407 |
| 2006/0257027 | A1* | 11/2006 | Hero et al. | 382/190 |
| 2008/0008401 | A1* | 1/2008 | Zhu et al. | 382/294 |
| 2008/0234578 | A1* | 9/2008 | Claus | 600/437 |
| 2009/0067752 | A1 | 3/2009 | Lee et al. | |

FOREIGN PATENT DOCUMENTS

| | | |
|---|---|---|
| JP | 10-255035 A | 9/1998 |
| JP | 2007-014525 A | 1/2007 |
| JP | 2009-071821 A | 4/2009 |
| KR | 10-2008-0053057 | 6/2008 |

OTHER PUBLICATIONS

Lange, et al. "Augmenting Intraoperative 3D Ultrasound with Preoperative Models for Navigation in Liver Surgery." *Lect Notes Comput SC*. (2004): 534-541.
Liu, et al. "Three-dimensional surface registration: A neural network strategy." *Neurocomputing*. 70. No. 1-3 (2006): 597-602.
Mostafa, et al. "Multimodality Image Registration and Fusion Using Neural Network." *Inform Fusion* Feb. 2000: WED3/3-WED3/9.
Wang, et al. "PET-MRI Image Registration and Fusion Using Artificial Neural Networks." *Biomed Eng-App Bas C*. 15. No. 3 (2003): 95-99.
Extended European Search Report issued in European Patent Application No. 09177188.1, dated Nov. 3, 2011.
Korean Office Action issued in Korean Patent Application No. KR 10-2009-0065664 dated Jun. 20, 2011.
Japanese Office Action with English translation issued in Japanese Application No. 2009-273780 mailed Oct. 8, 2013.

* cited by examiner

*Primary Examiner* — David Zarka
(74) *Attorney, Agent, or Firm* — McDermott Will & Emery LLP

(57) ABSTRACT

There are disclosed embodiments for image based registration. An image registration system sets image transform parameters based on pixels of registered ultrasound image and CT (or MRI) image. The image registration system transforms ultrasound images, which may be newly provided, by using the image transform parameters to thereby output transform images. The image registration system performs image based registration on the transform images and the second images.

10 Claims, 2 Drawing Sheets

IMAGE BASED REGISTRATION USING TRANSFORM AND SECOND IMAGES OF A TARGET OBJECT

The present application claims priority from Korean Patent Application Nos. 10-2008-0121461 filed on Dec. 2, 2008 and 10-2009-0065664 filed on Jul. 20, 2009, the entire subject matters of each of which are incorporated herein by reference.

TECHNICAL FIELD

The present disclosure relates to image registrations, and more particularly to image based registration between different types of images.

BACKGROUND

An ultrasound diagnostic system has been extensively used in the medical field due to its non-invasive and non-destructive nature. The ultrasound diagnostic system is highly safe and produces no dangerous side effects such as exposure to X-rays, etc. However, the ultrasound diagnostic system suffers from inherent shortcomings of an ultrasound image such as a low signal-to-noise ratio and a limited field of view. Thus, the image registration of a CT (or MR) image onto the ultrasound image has been introduced in order to compensate for deficiencies of the ultrasound image.

Conventionally, an image based registration using feature points extracted from the ultrasound image and the CT (or MR) image has been adopted for the image registration between the ultrasound image and the CT (or MR) image. This image registration may be implemented by matching the extracted feature points. However, this image based registration for registering the ultrasound image onto the CT (or MR) image is a difficult task due to their different imaging characteristics such as resolution, image quality, viewing angle, contrast, etc.

SUMMARY

Embodiments for performing image based registration on different types of images are disclosed herein. In one embodiment, by way of non-limiting example, an image registration system, comprises: a first image providing unit operable to provide first images of a target object; a second image providing unit operable to provide second images of the target object; and a processing unit operable to set image transform parameters based on pixels of the first and second images and transform the first images by using the image transform parameters to thereby output transform images, the processing unit being further operable to perform image registration on the transform images and the second images.

In another embodiment, an image registration method in an image registration system including a first image providing unit, a second image providing unit and a processing unit, comprises: a) at the first image providing unit, providing a first image of a target object; b) at the second image providing unit, providing a second image of the target object; c) at the processing unit, setting image transform parameters based on pixels of the first and second images; d) at the processing unit, transforming the first images by using the image transform parameters to thereby form transform images; and e) at the processing unit, performing image registration on the transform images and the second images.

In another embodiment, a computer-readable record medium storing instructions is configured to perform functions of: a) providing a first image of a target object; b) providing a second image of the target object; c) setting image transform parameters based on pixels of the first and second images; d) transforming the first images by using the image transform parameters to thereby form transform images; and e) performing image registration on the transform images and the second images.

The Summary is provided to introduce a selection of concepts in a simplified form that are further described below in the Detailed Description. This Summary is not intended to identify key or essential features of the claimed subject matter, nor is it intended to be used in determining the scope of the claimed subject matter.

DETAILED DESCRIPTION

A detailed description may be provided with reference to the accompanying drawings. One of ordinary skill in the art may realize that the following description is illustrative only and is not in any way limiting. Other embodiments of the present invention may readily suggest themselves to such skilled persons having the benefit of this disclosure.

Figure 1:
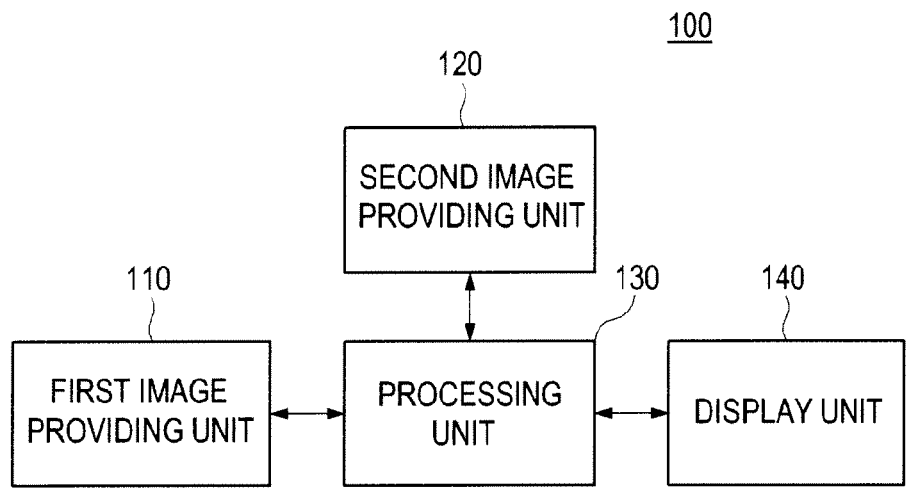
FIG. 1 is a block diagram showing an illustrative embodiment of an image registration system.

FIG. 1 is a block diagram showing an illustrative embodiment of an image registration system. Referring to FIG. 1, the image registration system 100 may include a first image providing unit 110, a second image providing unit 120, a processing unit 130 and a display unit 140.

The first image providing unit 110 may be operable to provide first images of a target object. The first image providing unit 110 may be embodied with an ultrasound diagnostic device. The ultrasound diagnostic device may be operable to transmit ultrasound signals to the target object and receive ultrasound echo signals. The ultrasound diagnostic device may be operable to form the first images based on the receive ultrasound echo signals. In one embodiment, the first images may include at least one of a 2-dimensional ultrasound image and a 3-dimensional ultrasound image.

Figure 2:
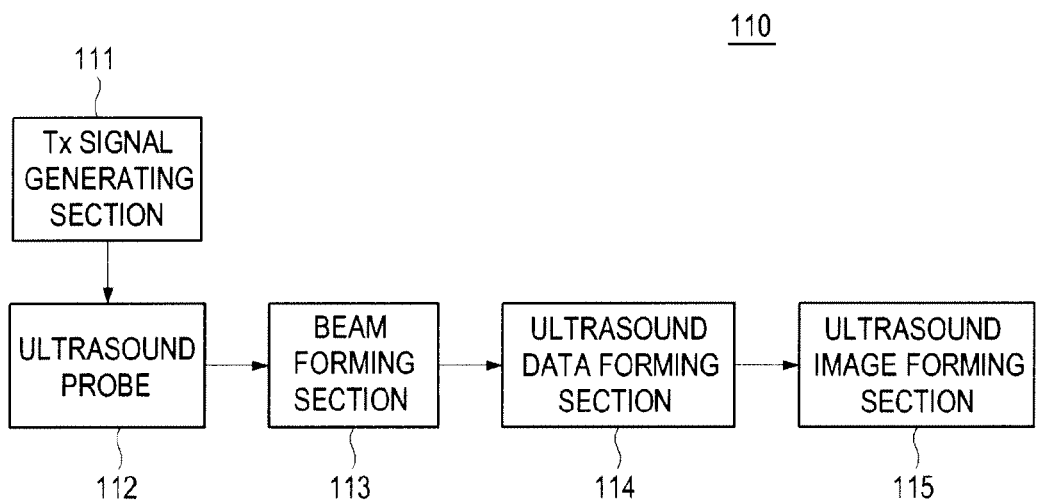
FIG. 2 is a block diagram showing an illustrative embodiment of a first image providing unit.

FIG. 2 is a block diagram showing an illustrative embodiment of the first image providing unit 110. Referring to FIG. 2, the first image providing unit 110 may include a transmit (Tx) signal generating section 111 that may be operable to generate a plurality of Tx signals. The first image providing unit 110 may further include an ultrasound probe 112 coupled to the Tx signal generating section 111. The ultrasound probe 112 may contain an array transducer consisting of a plurality of transducer elements (not shown). The ultrasound probe 112 may be operable to transmit ultrasound signals to the target object in response to the Tx signals. The ultrasound probe 112 may be further operable to receive echo signals reflected from the target object to thereby form electrical receive signals. The ultrasound probe 112 may include a convex probe, a linear probe, etc., but is not limited thereto.

The first image providing unit 110 may further include a beam forming section 113. The beam forming section 113 may be operable to apply delays to the electrical receive signals in consideration of positions of the transducer elements and focal points. The beam forming section 113 may further be operable to sum the delayed receive signals to thereby output a plurality of receive-focused beams.

The first image providing unit 110 may further include an ultrasound data forming section 114 that may be operable to form the ultrasound data corresponding to a plurality of consecutive frames based on the receive-focused beams. The ultrasound data forming section 114 may be further operable to perform signal processing, such as gain adjustment, filtering, etc., upon the receive-focused beams.

The first image providing unit 110 may further include an ultrasound image forming section 115 that may be operable to form ultrasound images based on the ultrasound data. The image forming section 115 may be operable to perform image processing for further image optimization.

Referring back to FIG. 1, the second image providing unit 120 may be operable to provide second images of the target object. The second images may be different types from the first images. The second image providing unit 120 may include one of a magnetic resonance imaging (MRI) diagnostic device for providing MRI images and a computerized tomography (CT) scanner for providing CT images. In one embodiment, although it is described that the first images are ultrasound images and the second images are CT images (or MRI images), the first and second images are not limited thereto. For example, the first images may be CT images (or MRI images) and second image may be an ultrasound image.

The processing unit 130 may be coupled to the first and second image providing units 110 and 120 to receive the first and second images. The processing unit 130 may be operable to set image transform parameters necessary for image transform. The setting of the image transform parameters will be described in detail later. The processing unit 130 may be further operable to transform the first images by using the set image transform parameters to thereby form transform images. The processing unit 130 may be further operable to perform image based registration upon the transform images and the second images.

Figure 3:
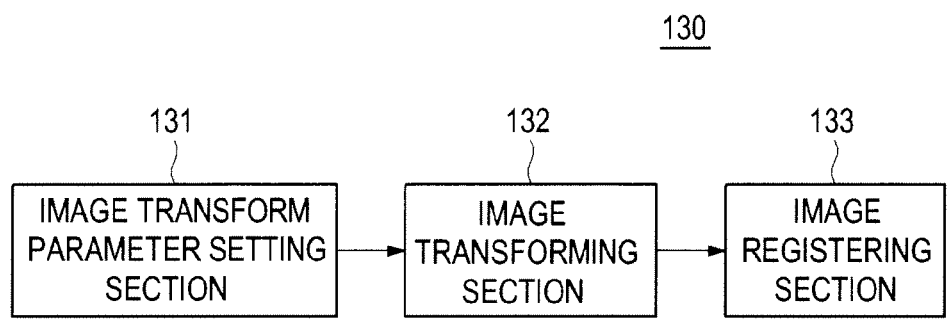
FIG. 3 is a block diagram showing an illustrative embodiment of a processing unit.

FIG. 3 is a block diagram showing an illustrative embodiment of the processing unit 130. As shown in FIG. 3, the processing unit 130 may include an image transform parameter setting section 131, an image transforming section 132 and an image registering section 133.

The image transform parameter setting section 131 may be operable to perform image registration on at least one of the first images and at least one of the second images to thereby output registered first and second images. The image registration may be carried out by using one of the well-known image registration methods to a person skilled in the art. Thus, the detailed description thereof will be omitted. The image transform parameter setting section 131 may be operable to select a plurality of pixel data sets from the registered first and second images. The image transform parameter setting section 131 may be operable to set the image transform parameters by using the neural network algorithm including the back-propagation algorithm based on the selected pixel data sets.

Figure 4:
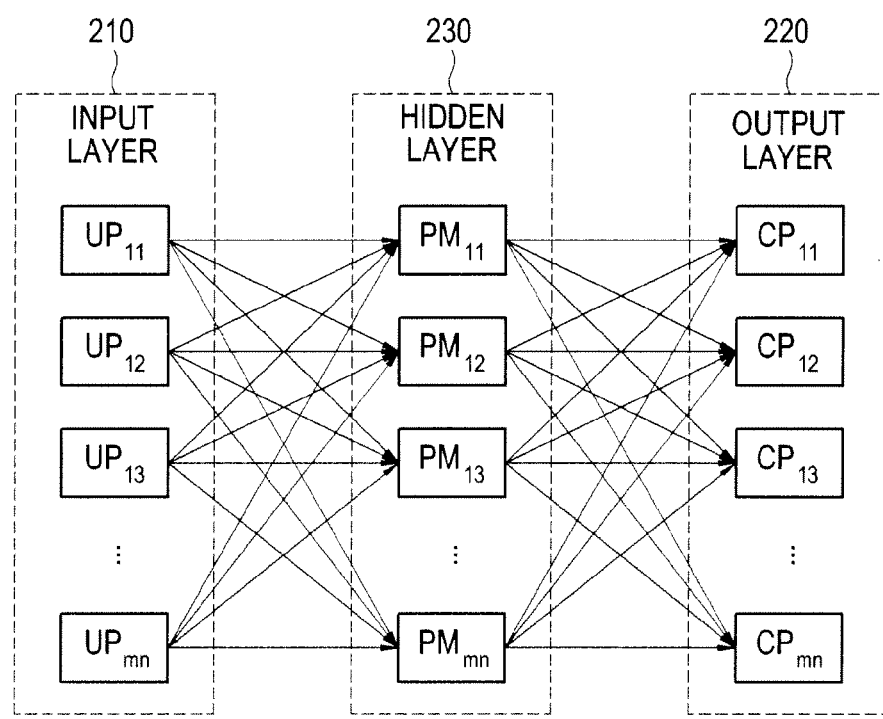
FIG. 4 is a schematic diagram showing an example of a neural network algorithm to set image transform parameters.

Hereinafter, the setting of the image transform parameters using the neural network algorithm will be described in detail with reference to FIG. 4. The image transform parameter setting section 131 may be operable to set pixels $UP_{11}$-$UP_{mn}$ of the registered first image as an input layer 210 and pixels $CP_{11}$-$CP_{mn}$ of the registered second image as an output layer 220, as illustrated in FIG. 4. The image transform parameter setting section 131 may be operable to perform a multiplicity of predetermined operations such as multiplication, addition, etc., upon the pixels $UP_{11}$-$UP_{mn}$ of the registered first image at a hidden layer 230. That is, the image transform parameter setting section 131 may be operable to apply image transform parameters $PM_{11}$-$PM_{mn}$ to the pixels $UP_{11}$-$UP_{mn}$ of the registered first image to thereby form transformed pixels corresponding to the pixels $UP_{11}$-$UP_{mn}$ of the registered first image.

Further, the image transform parameter setting section 131 may be operable to compare the transformed pixels with the pixels $CP_{11}$-$CP_{mn}$ of the registered second image to calculate errors therebetween. If the calculated errors are greater than a predetermined threshold, the image transform parameter setting section 131 may be operable to update the image transform parameters $PM_{11}$-$PM_{mn}$ in proportion to the calculated errors. In one embodiment, by way of non-limiting example, the image transform parameters $PM_{11}$-$PM_{mn}$ may be updated by using a gradient descent method. The image transform parameter setting section 131 may be operable to perform a multiplicity of predetermined operations, for example, applying the updated image transform parameters to the pixels $UP_{11}$-$UP_{mn}$ of the registered first image to thereby form transformed pixels. The image transform parameter setting section 131 may be further operable to calculate errors between the transformed pixels and the pixels $CP_{11}$-$CP_{mn}$ of the registered second image. If the calculated errors are greater than a predetermined threshold, the image transform parameter setting section 131 may be operable to update the image transform parameters $PM_{11}$-$PM_{mn}$ in proportion to the calculated errors. The above process is repeatedly carried out until the errors become less than the predetermined threshold, so that the image transform parameters can be set. That is, if the errors are less than the predetermined threshold, the image transform parameter setting section 131 may be operable to finally set image transform parameters.

The image transforming section 132 may be operable to perform image transformation upon first images, which are provided from the first image providing unit 110, by using the image transform parameters set by the image transform parameter setting section 131, thereby forming transform images. For example, the image transforming section 132 may be operable to perform a multiplicity of predetermined operations upon the first images by using the set image transform parameters to thereby form the transform images.

The image registering section 133 may be operable to perform image registration between the transform images and the second images to thereby output registration images. In one embodiment, by way of non-limiting example, the image registering section 133 may be operable to analyze the transform images and the second images to extract feature points, and perform the image registration by using the extracted feature points. Since the image based registration is carried out upon the transform images, which are similar to the second image, the image registration may be easily and accurately implemented.

Referring back to FIG. 1, the display unit 140 may display the registered transform images and the second images. The display unit 140 may further display the first images and the registration images.

In another embodiment, a computer-readable record medium storing instructions is configured to perform functions of: a) providing a first image of a target object; b) providing a second image of the target object; c) setting image transform parameters based on pixels of the first and second images; d) transforming the first images by using the image transform parameters to thereby form transform images; and e) performing image registration on the transform images and the second images.

Although embodiments have been described with reference to a number of illustrative embodiments thereof, it should be understood that numerous other modifications and embodiments can be devised by those skilled in the art that will fall within the spirit and scope of the principles of this disclosure. More particularly, numerous variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. An image registration apparatus, comprising:
a processing unit coupled to a first image providing unit; and
a second image providing unit configured to receive first images and second images of a target object, modalities of the first images being different from modalities of the second images, wherein:
the processing unit is configured to:
perform a first image registration on at least one of the first images and on at least one of the second images;
set image transform parameters by selecting a plurality of pixel data sets from the registered first and second images and using a back-propagation algorithm based on the selected pixel data sets; and
apply the image transform parameters to pixels of the first images to output transformed images having imaging characteristics similar to imaging characteristics of the second images, and
the processing unit is further configured to perform a second image registration on the transformed images and the second images to output registration image.

2. The system of claim 1, wherein the first images include ultrasound images and the second images include magnetic resonance imaging (MRI) images or computerized tomography (CT) images.

3. The system of claim 1, wherein the first images include magnetic resonance imaging (MRI) images or computerized tomography (CT) images, and the second images include ultrasound images.

4. The system of claim 1, further comprising a display unit for displaying the registration images.

5. An image registration method in an image registration apparatus, performed by a processing unit coupled to a first image providing unit for receiving first images of a target object, and to a second image providing unit for receiving second images of the target object, modalities of the first images being different from modalities of the second images, the method comprising steps of:

a) performing, by the processing unit, a first image registration on at least one of the first images and on at least one of the second images, and setting image transform parameters by selecting a plurality of pixel data sets from the registered first and second images and using a back-propagation algorithm based on the selected pixel data sets;
b) applying, by the processing unit, the image transform parameters to the pixels of the registered first image to output transformed images having imaging characteristics similar to imaging characteristics of the second images; and
c) performing, by the processing unit, a second image registration on the transformed images and the second images to output registration images.

6. The image registration method of claim 5, wherein the first images include ultrasound images and the second images include magnetic resonance imaging (MRI) images or computerized tomography (CT) images.

7. The image registration method of claim 5, wherein the first images include magnetic resonance imaging (MRI) images or computerized tomography (CT) images, and the second images include ultrasound images.

8. The image registration method of claim 5, wherein the step d) includes applying the image transform parameters to the first images to form the transformed images.

9. The image registration method of claim 5, further comprising displaying the registration images.

10. A non-transitory computer-readable record medium, storing instructions which cause a processing unit to perform the following functions of:
a) providing a first image of a target object;
b) providing a second image of the target object, a modality of the first image being different from a modality of the second image;
c) performing a first image registration on at least one of the first images and at least one of the second images based on pixels of the first and second images, and setting image transform parameters by selecting a plurality of pixel data sets from the registered first and second images and using a back-propagation algorithm based on the selected pixel data sets;
d) applying the image transform parameters to the pixels of the registered first image to output transformed images having imaging characteristics similar to imaging characteristics of the second images; and
e) performing image registration on the transformed images and the second images.

* * * * *